(12) United States Patent
Randle et al.

(10) Patent No.: US 11,116,588 B2
(45) Date of Patent: Sep. 14, 2021

(54) FLEXIBLE ROBOTIC SURGICAL INSTRUMENT

(71) Applicant: CMR SURGICAL LIMITED, Cambridge (GB)

(72) Inventors: Steven James Randle, Stratford-upon-Avon (GB); Luke David Ronald Hares, Cambridge (GB); Keith Marshall, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 682 days.

(21) Appl. No.: 15/744,233

(22) PCT Filed: Jul. 6, 2016

(86) PCT No.: PCT/GB2016/052027
§ 371 (c)(1),
(2) Date: Jan. 12, 2018

(87) PCT Pub. No.: WO2017/009604
PCT Pub. Date: Jan. 19, 2017

(65) Prior Publication Data
US 2018/0200005 A1    Jul. 19, 2018

(30) Foreign Application Priority Data
Jul. 13, 2015   (GB) ..................... 1512227

(51) Int. Cl.
*A61B 34/30* (2016.01)
*A61B 17/00* (2006.01)

(52) U.S. Cl.
CPC ........ *A61B 34/30* (2016.02); *A61B 2017/003* (2013.01); *A61B 2034/305* (2016.02); *A61B 2034/306* (2016.02)

(58) Field of Classification Search
CPC .............. A61B 34/30; A61B 2034/305; A61B 2034/306; A61B 2017/003
(Continued)

(56) References Cited

U.S. PATENT DOCUMENTS 5,271,381 A     12/1993  Ailinger
2006/0199999 A1*  9/2006  Ikeda ................. A61B 1/00149
                                                      600/141
(Continued)

FOREIGN PATENT DOCUMENTS

CN    102028545 B    5/2017
EP    2361577        8/2011
(Continued)

OTHER PUBLICATIONS

Japanese Office Action dated Aug. 24, 2020 in JP Application No. 2018-501247.
(Continued)

*Primary Examiner* — Aaron F Roane
(74) *Attorney, Agent, or Firm* — Occhiuti & Rohlicek LLP

(57) ABSTRACT

A robotic surgical instrument comprising a shaft, an articulated section and a drive mechanism. The articulated section extends from the shaft and terminates at its distal end in a tip. The tip has an attachment for an end effector. The drive mechanism drives the articulated section via flexible driving elements thereby altering the angular orientation of the tip relative to the shaft. The drive mechanism is controlled so as to always fully compress the articulated section along at least one extent by which the articulated section connects the tip and the shaft whilst driving the articulated section from any one configuration to any other configuration. The drive
(Continued)

mechanism constrains movement of the articulated section so as to permit the tip to move with two degrees of rotational freedom and no degrees of translational freedom relative to the shaft.

13 Claims, 6 Drawing Sheets

(58) Field of Classification Search
USPC .............................................................. 606/1
See application file for complete search history.

(56) References Cited

U.S. PATENT DOCUMENTS

| | | |
|---|---|---|
| 2008/0287741 A1 | 11/2008 | Bean et al. |
| 2009/0024141 A1 | 1/2009 | Stahler |
| 2010/0160929 A1* | 6/2010 | Rogers .................. A61B 34/71 606/130 |
| 2011/0106141 A1 | 5/2011 | Nakamura |
| 2013/0023915 A1 | 1/2013 | Mueller |
| 2014/0371764 A1* | 12/2014 | Oyola ..................... B25J 9/065 606/130 |

FOREIGN PATENT DOCUMENTS

| | | |
|---|---|---|
| EP | 2674110 | 12/2013 |
| JP | 2008-531222 A | 8/2008 |
| JP | 2011-092743 A | 5/2011 |
| WO | 2006094242 A1 | 9/2006 |
| WO | WO2009/108674 | 9/2009 |
| WO | 2010109932 A1 | 9/2010 |
| WO | WO2012/126783 | 9/2012 |
| WO | WO2013/039999 | 3/2013 |

OTHER PUBLICATIONS

Japanese Notification of Reasons for Refusal dated Jan. 20, 2021 in JP Application No. 2018-501247.
Chinese Office Action dated Dec. 2, 2020 in CN Application No. 201680041323.2.

* cited by examiner

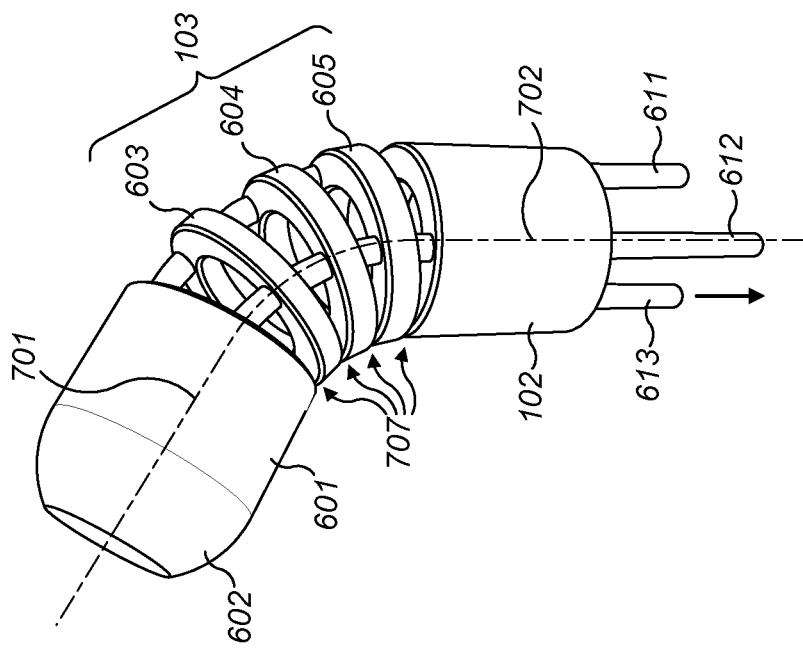
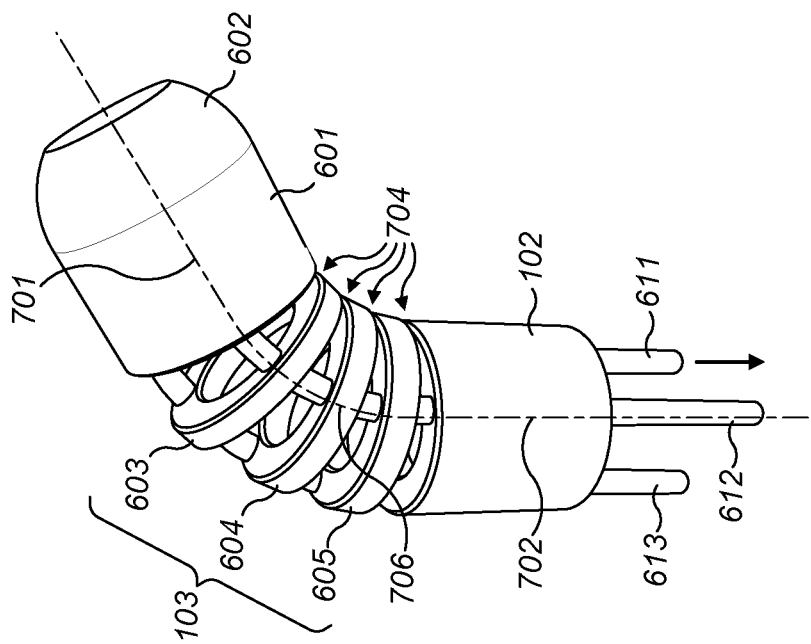

FLEXIBLE ROBOTIC SURGICAL INSTRUMENT

CROSS REFERENCE TO RELATED APPLICATIONS

This application is a National Stage of International Application No. PCT/GB2016/052027 filed on Jul. 6, 2016, which claims priority to Great Britain Application No. 1512227.8 filed on Jul. 13, 2015, the contents of which are hereby incorporated by reference in their entireties.

BACKGROUND

It is known to use robots for assisting and performing surgery. Surgical robots normally consist of a base, an arm, and an instrument. The base supports the robot, and is itself attached rigidly to, for example, the operating theatre floor, the operating theatre ceiling or a trolley. The arm extends between the base and the instrument. The arm typically has a plurality of articulations, which are used to locate the surgical instrument in a desired location relative to the patient. The surgical instrument is attached to the distal end of the robot arm. The surgical instrument penetrates the body of the patient at a port so as to access the surgical site.

FIG. 1 illustrates a typical surgical instrument 100 for performing robotic laparoscopic surgery. The surgical instrument comprises a base 101 by which the surgical instrument connects to the robot arm. A shaft 102 extends between base 101 and articulated portion 103. Articulated portion 103 terminates in an end effector 104. In FIG. 1, a pair of serrated jaws are illustrated as the end effector 104. The articulated portion 103 permits the end effector 104 to move relative to the shaft 102. It is desirable for at least two degrees of freedom to be provided to the motion of the end effector 104 by means of the articulated portion.

FIG. 2 illustrates an example of a known surgical instrument 200 in which end effector 104 is permitted to move relative to shaft 102 by means of pitch joint 201 and yaw joint 202. Joint 201 enables the end effector 104 to rotate about pitch axis 203. Joint 202 enables the end effector 104 to rotate about yaw axis 204. The articulated portion requires many precisely made elements. It also requires two cables per joint and the cables needed to articulate the end effector to all fit within the articulated portion without catching on each other in any configuration of the articulated portion and end effector. Pulleys, such as pulley 205 are used to manage the cables in this manner. The external diameter of the shaft is 8 mm in order to accommodate the number and size of the internal elements of the articulated portion. It is desirable to reduce the external diameter of the shaft in order to minimise the size of the incision through the skin of the patient and disruption inside the patient's body.

FIG. 3 illustrates another example of a known surgical instrument 300 in which end effector 104 is permitted to move relative to shaft 102 by means of articulated portion 103. Articulated portion 103 is a flexible section in which two degrees of freedom of the end effector 104 are enabled over the course of four joints 301, 302, 303 and 304. Each joint is controlled independently by a pair of cables. The flexible section 103 is more compact than that of FIG. 2, and hence the external diameter of the shaft is reduced compared to FIG. 2. However, the flexible section 103 requires many precisely made very small elements. Additionally, five pairs of cables are required to articulate the joints of the flexible portion and the end effector 104. A less complex articulation would be preferable.

FIG. 4 illustrates a further example of a known surgical instrument 400 in which the articulated portion 103 is flexible. Two degrees of freedom of the end effector 104 are enabled over the course of the flexible section using four cables. This is less complex than the articulation of FIG. 3. However, this configuration is not precisely controllable, as will be explained with reference to FIGS. 5a, 5b and 5c. FIGS. 5a, 5b, and 5c illustrate an articulated section 103 connected at one end to shaft 102 and at the other to instrument tip 501. Two cables 502 and 503 are illustrated. These cables enable actuation of the instrument tip about one axis. Two further cables enabling actuation of the instrument tip about another axis are not shown here for ease of illustration. The cables 501 and 502 engage with the flexible section. When cable 502 is placed under tension and cable 503 released, the instrument tip 501 bends to one side as shown in FIG. 5b. This articulated section arrangement is thus able to articulate the instrument tip. However, the instrument tip is not precisely controlled. For example, FIG. 5c illustrates a scenario in which both the cables 502 and 503 have the same length, however the instrument tip 501 is not collinear with the instrument shaft 102.

It is known to solve the misalignment problem of FIG. 5c by making the articulated section sprung. The misaligned configuration of FIG. 5c is energetically unfavourable compared to the aligned configuration of FIG. 5a. Thus, by making the articulated section sprung, the flexible section of the surgical instrument of FIG. 4 becomes more controllable. However, the size of the sprung force required to reliably control the articulated section depends on the magnitude and direction of the loads applied to the surgical instrument. A doubling or tripling of the force to actuate the joint compared to a non-sprung joint is typically required.

SUMMARY OF THE INVENTION

According to an aspect of the invention, there is provided a robotic surgical instrument comprising: a shaft; an articulated section extending from the shaft and terminating at its distal end in a tip, the tip having an attachment for an end effector; and a drive mechanism configured to drive the articulated section via flexible driving elements thereby altering the angular orientation of the tip relative to the shaft, wherein the drive mechanism is configured to be controlled so as to always fully compress the articulated section along at least one extent by which the articulated section connects the tip and the shaft whilst driving the articulated section from any one configuration to any other configuration, and wherein the drive mechanism is configured to constrain movement of the articulated section so as to permit the tip to move with two degrees of rotational freedom and no degrees of translational freedom relative to the shaft.

The drive mechanism may constrain movement of the articulated section so as to permit the tip to rotate about axes in a plane transverse to the longitudinal axis of the shaft.

The flexible driving elements may extend through the shaft, engage with the articulated section and terminate in the tip.

The drive mechanism may be configured to always retain at least one flexible driving element in full tension.

Suitably, in a configuration in which the longitudinal axis of the tip is collinear with the longitudinal axis of the shaft, the drive mechanism is configured to retain all the flexible driving elements in full tension.

Suitably, in a configuration in which the longitudinal axis of the tip is not collinear with the longitudinal axis of the shaft, the drive mechanism is configured to retain only one flexible driving element in full tension. Suitably in this configuration, the drive mechanism is configured to retain at least one other flexible driving element in compression.

Suitably, the flexible driving elements resist compression and tension forces.

Suitably, the robotic surgical instrument comprises at least three flexible driving elements.

Suitably, the articulated section comprises a series of annular rings connected to each other by the flexible driving elements. The annular rings may be connected to the shaft and the tip by the flexible driving elements. Suitably, in a configuration in which the longitudinal axis of the tip is collinear with the longitudinal axis of the shaft, the annular rings are stacked such that their centres lie on an axis which is collinear with the longitudinal axes of the shaft and tip. In the said configuration, the facing surfaces of adjacent annular rings may be in full contact.

In a configuration in which the longitudinal axis of the tip is offset angularly from the longitudinal axis of the shaft, the facing surfaces of adjacent annular rings may contact each other at only one point.

The annular rings may be sprung apart from each other.

The articulated section may comprise a single-start helical cut spring. The articulated section may comprise a multi-start helical cut spring.

The robotic surgical instrument may further comprise strain gauges, each strain gauge configured to measure the tension on a respective flexible driving element.

The drive mechanism may be configured to displace a flexible driving element until that flexible driving element has a desired tension. The drive mechanism may be configured to receive the desired tension from a controller, the desired tension determined according to a model of the current and desired orientations of the tip and the tensions of the flexible driving elements.

The robotic surgical instrument may further comprise contact sensors for detecting contact between facing surfaces of adjacent annular rings.

Suitably, the drive mechanism is configured to displace a flexible driving element until contact is detected between facing surfaces of adjacent annular rings by the contact sensors.

BRIEF DESCRIPTION OF THE FIGURES

The present invention will now be described by way of example with reference to the accompanying drawings. In the drawings:

FIGS. 7a, 7b and 7c illustrate different configurations of the surgical instrument of FIG. 6.

DETAILED DESCRIPTION

Figure 1:
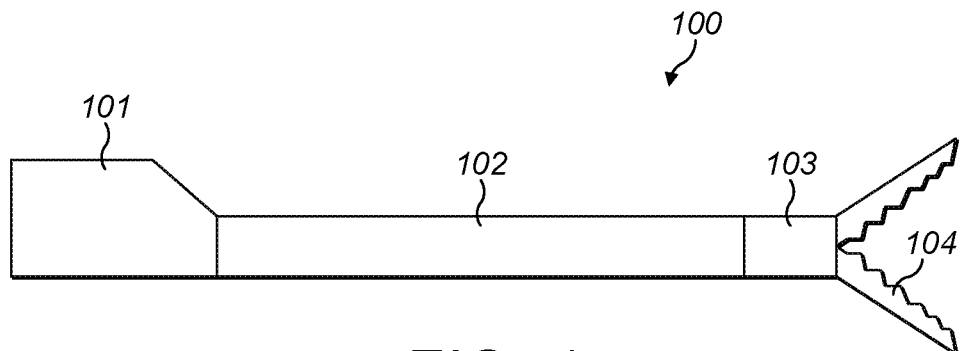
FIG. 1 illustrates a known robotic surgical instrument.
Figure 2:
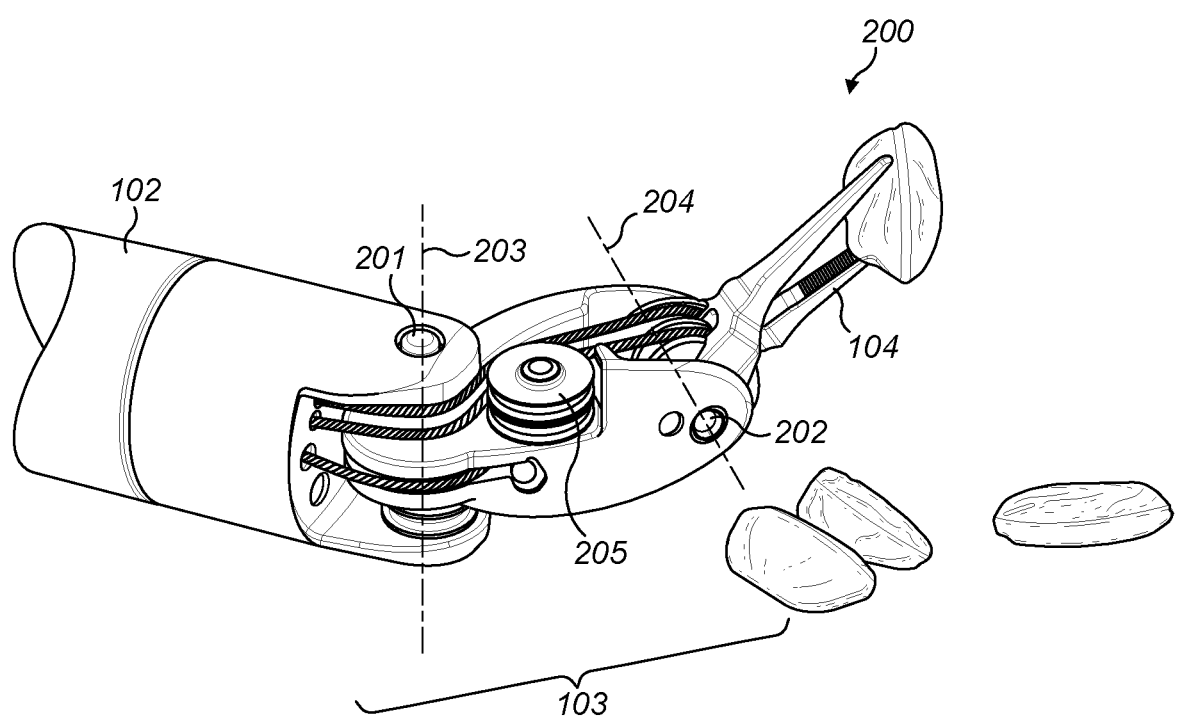
FIG. 2 illustrates a known robotic surgical instrument having two separated joints.
Figure 6:
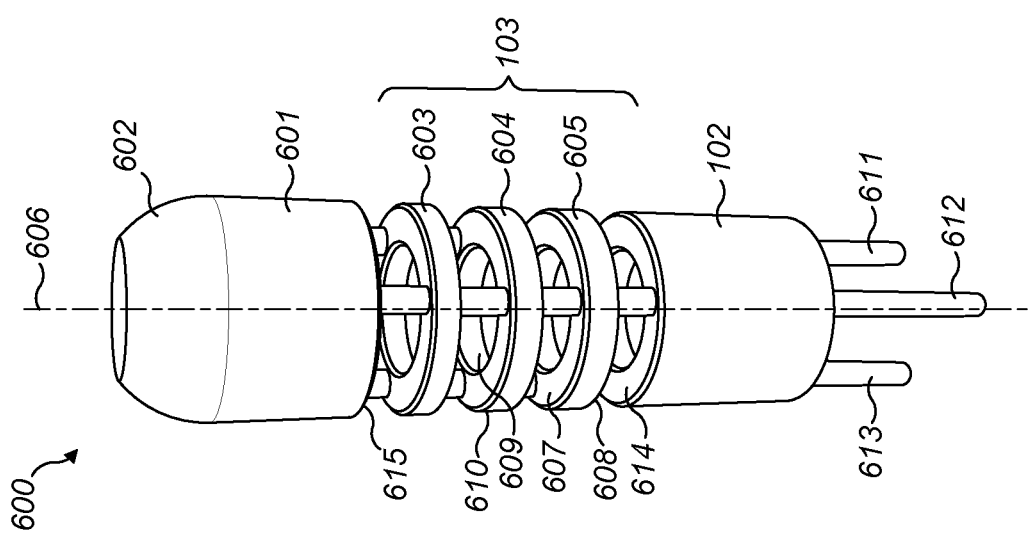
FIG. 6 illustrates the distal end of a surgical instrument.

FIG. 6 illustrates the distal end of a surgical instrument. The surgical instrument as a whole has the general form shown in FIG. 1. In other words, the surgical instrument comprises a base 101 by which the surgical instrument connects to the surgical robot arm. The instrument base is designed cooperatively with the terminal end of the surgical robot arm, such that the instrument base is releasably attachable to the terminal end of the robot arm. A shaft 102 extends between the base 101 and an articulated section 103. The articulated section 103 is connected at its proximal end to the shaft 102 and at its distal end to the instrument tip 601. The instrument tip 601 has an attachment 602 suitable for attaching an end effector 104. The shaft 102, articulated section 103 and instrument tip 601 are all hollow. This allows passage of elements up these sections to actuate the end effector 104. It also reduces the weight of the surgical instrument.

The end effector may take any suitable form. For example, the end effector may be smooth jaws, serrated jaws, a gripper, a pair of shears, a needle for suturing, a camera, a laser, a knife, a stapler, a cauteriser, a suctioner.

The articulated section 103 is flexible. Suitably, the articulated section 103 is not sprung. Alternatively, the articulated section 103 may be lightly sprung. The articulated section 103 of FIG. 6 comprises a set of annular rings 603, 604, 605 and driving elements 611, 612 and 613.

Three annular rings are depicted in FIG. 6, however it will be understood that fewer or more annular rings may be used. The annular rings are not rigidly attached to each other. The annular rings are stacked such that when the instrument is in a straight configuration in which the tip is collinear with the shaft as shown in FIG. 6, the centres of the annular rings lie on the longitudinal axis 606 of the instrument. Each annular ring comprises: a first surface 607 bounded by the inner and outer concentric rings of the annulus; a second surface 608 opposite the first surface and also bounded by the inner and outer concentric rings of the annulus; an inner surface 609 bounded by the inner concentric ring of the annulus and perpendicular to the first and second surfaces; and an outer surface 610 bounded by the outer concentric ring of the annulus and also perpendicular to the first and second surfaces. The outer surfaces of the annular rings are aligned with the exterior surfaces of the shaft and tip. The outer surfaces of the annular rings are flush with the exterior surfaces of the shaft and tip. For each annular ring, its first surface faces the second surface of the adjacent annular ring stacked on one side of it, and its second surface faces the first surface of the adjacent annular ring stacked on the other side of it. The exceptions to this are the annular rings at either end of the articulated section 103, one of which faces an annular ring 614 on the terminal end of the shaft 102, the other of which faces an annular ring 615 on the proximal end of the instrument tip 601.

The inner and outer concentric rings of the annular rings shown in FIG. 6 are circular. The inner and outer rings may have a non-circular profile. For example, they may be oval or ellipse shaped. Suitably, the outer ring of the annular rings matches the profile of the outside of the shaft. Thus, if the shaft is circular in cross-section, the outer ring of the annular rings is a matching circular shape and size to that of the shaft. This provides a smooth exterior profile to the instrument which is less likely to get caught or snag in the surgical site.

The annular rings are connected to each other by the driving elements. Each driving element engages with each of the annular rings. In the arrangement shown in FIG. 6, each driving element passes through an opening in each annular ring. That opening penetrates the annular ring through the first surface and second surface of the annular ring perpendicular to the first and second surfaces. The annular rings are not secured to the driving elements. The annular rings are free to slide along the driving elements. However, the motion of each annular ring is constrained by virtue of the driving elements which are passing through it. Thus, the driving elements prevent the annular rings from detaching from the surgical instrument. The annular rings are connected to the shaft and the tip by the driving elements. Each driving element passes through the annular ring 614 at the distal end of the shaft, through each of the annular rings in the flexible section, and through the annular ring 615 at the proximal end of the instrument tip 601. The proximal ends of the driving elements are connected to a drive mechanism in the base of the surgical instrument. The driving elements extend through the shaft 102, through the flexible section 103 and into the instrument tip 601. The distal ends of the driving elements are secured to the instrument tip.

The driving elements are flexible. Each driving element is elongate. Each driving element is linear when at rest. In other words, each driving element is linear when in an unstrained state, when no external forces are being applied to it. Each driving element can be flexed laterally to its main extent. In other words, each driving element can be flexed transversely to its longitudinal axis. Each driving element is not flexible along its main extent. Each driving element resists compression and tension forces acting in the direction of its longitudinal axis.

Thus, the driving elements are able to transfer drive from the base of the instrument to the instrument tip. The driving elements may be rods. For example, the driving elements may be push/pull rods. The driving elements may be cables. The driving elements may be fabricated from a spring steel. Alternatively, the driving elements may be fabricated from a composite such as carbon fibre.

The driving elements are secured in the base of the instrument in such a way that they can be put under tension, and optionally also under compression. For example, a driving element may be secured to a plate. A screw is threaded through the plate. A motor drives rotation of the screw. By tightening the screw, the plate moves towards the proximal end of the instrument (i.e. towards the robot arm), thereby pulling the driving element. By loosening the screw, the plate moves towards the distal end of the instrument (i.e. towards the instrument tip), thereby pushing the driving element. As another example, a driving element may each be secured to a spool. A motor drives rotation of the spool. By rotating the spool in one direction, the driving element winds around the spool, thereby shortening the length of the driving element in the shaft and articulated portion. In other words, this action provides a tensioning or pulling force on the driving element. By rotating the spool in the other direction, the driving element unwinds around the spool, thereby increasing the length of the driving element in the shaft and articulated portion. In other words, this action provides a compressing or pushing force on the driving element.

When a driving element is pulled towards the instrument base, since the driving element is secured to the instrument tip, it pulls the instrument tip in the direction of the applied tension. In other words, it pulls the instrument tip towards the instrument base. This causes the articulated section 103 to compress in the region of that driving element. In the example of FIG. 6, the shaft and instrument tip are rigid and fixed in length but the annular rings are slideable along the driving element. Thus, as a driving element is pulled, that driving element slides through the annular rings that it is engaged with, thereby pulling the annular rings that it passes through together. The stack of annular rings that the driving element passes through is thereby compressed.

When a driving element is pushed away from the instrument base, since the driving element is secured to the instrument tip, it pushes the instrument tip in the direction of the applied compression. In other words, it pushes the instrument tip away from the instrument base. This causes the articulated section 103 to extend in the region of that driving element. In the example of FIG. 6, as a driving element is pushed, that driving element slides through the annular rings that it is engaged with, thereby pushing the annular rings that it passes through apart from each other. The stack of annular rings that the driving element passes through is thereby extended.

Figure 7A:
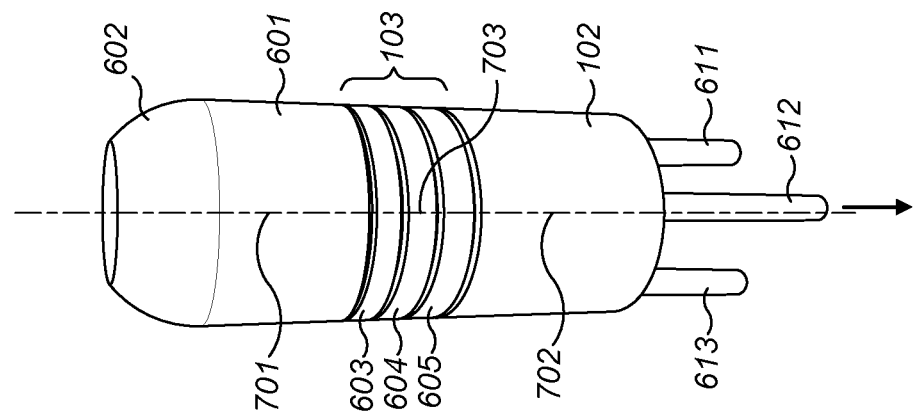

FIG. 6 illustrates a surgical instrument having three driving elements which engage with the articulated section 103 and the instrument tip 601 to orientate the instrument tip. Alternatively, four driving elements may be used. Further driving elements may also be used. At least three driving elements are used to enable the instrument tip to be orientated with two degrees of rotational freedom relative to the shaft 102. FIGS. 7*a*, 7*b* and 7*c* illustrate three arrangements of the driving elements which cause three different orientations of the instrument tip.

FIG. 7*a* illustrates a straight configuration of the surgical instrument. In this configuration the longitudinal axis 701 of the instrument tip is collinear with the longitudinal axis 702 of the shaft. In this configuration, the drive mechanism in the base of the instrument retains all the driving elements in full tension. Thus, in the example of FIG. 7*a*, all three driving elements 611, 612 and 613 are pulled. This causes the articulated section 103 to fully compress. The annular rings stack on top of each other. The centres of the annular rings lie on an axis 703 which is collinear with the longitudinal axes of the instrument tip 701 and the shaft 702. The facing surfaces of adjacent annular rings are in full contact. In other words, for each annular ring, its first surface contacts the second surface of the adjacent annular ring over its entire first surface. Similarly, for that annular ring, its second surface contacts the first surface of the adjacent annular ring over its entire second surface. For the annular ring at the shaft end of the articulated section, its surface facing the shaft surface 614 is in full contact with the shaft surface 614. For the annular ring at the tip end of the articulated section, its surface facing the tip surface 615 is in full contact with the tip surface 615.

FIG. 7*b* illustrates a first bent configuration of the surgical instrument. In this configuration the longitudinal axis 701 of the instrument tip is not collinear with the longitudinal axis 702 of the shaft. The longitudinal axis 701 of the instrument tip is offset angularly from the longitudinal axis 702 of the shaft. The drive mechanism in the base of the instrument retains only one driving element in full tension. In FIG. 7*b*, this is driving element 611. Driving element 611 is pulled, which causes articulated section 103 to fully compress in the region of that driving element. The facing surfaces of adjacent annular rings contact only at one contact point 704. This contact point is at the exterior edges of the facing surfaces of the adjacent annular rings closest to the driving element under tension. The facing surfaces of the annular rings are no longer equally spaced across their surfaces as in FIG. 7*a*. The facing surfaces of the annular rings are not parallel to each other as in FIG. 7*a*. The separation between the facing surfaces of adjacent annular rings increases from nothing at the contact point 704, to a larger separation 705 at the opposite exterior edge. The instrument tip is thereby oriented into the first bent configuration shown. The centres of the annular rings lie on a uniform curve 706 which joins the longitudinal axis 701 of the instrument tip to the longitudinal axis 702 of the shaft.

The other driving elements may be put under no forces by the drive mechanism. Alternatively, one or more of the other driving elements may be pushed by the drive mechanism. By retaining the one or more other driving elements 612, 613 in compression in addition to retaining the driving element 611 in tension, the configuration of the articulated section and instrument tip is more rigid. This provides extra stability to the position of the end effectors. Extra security and stability in the position of the end effectors is useful if they are to put the surgical instrument under stress, for example if a load is applied to the end effectors.

FIG. 7*c* illustrates a second bent configuration of the surgical instrument. In this configuration, the instrument tip is bent to the opposite side to that illustrated in FIG. 7*b*. The same principles apply as discussed above in relation to FIG. 7*b*. This time, only driving element 613 is in full tension. The facing surfaces of adjacent annular rings contact only at contact point 707. Contact point 707 is at the exterior edges of the facing surfaces of the adjacent annular rings closest to the driving element 613.

Figure 5C:
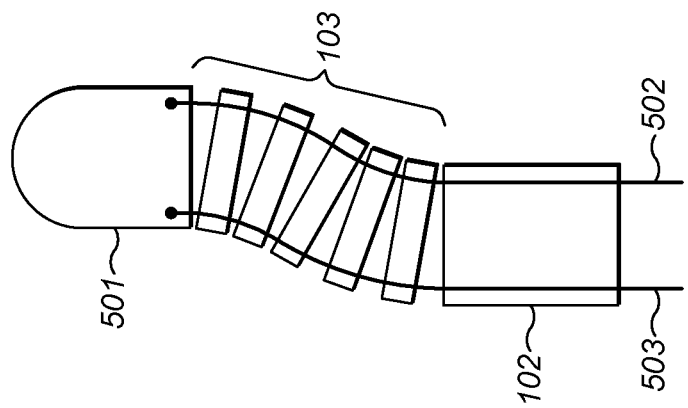
FIGS. 5a, 5b and 5c illustrate different configurations of a flexible section of a robotic surgical instrument.
Figure 5B:
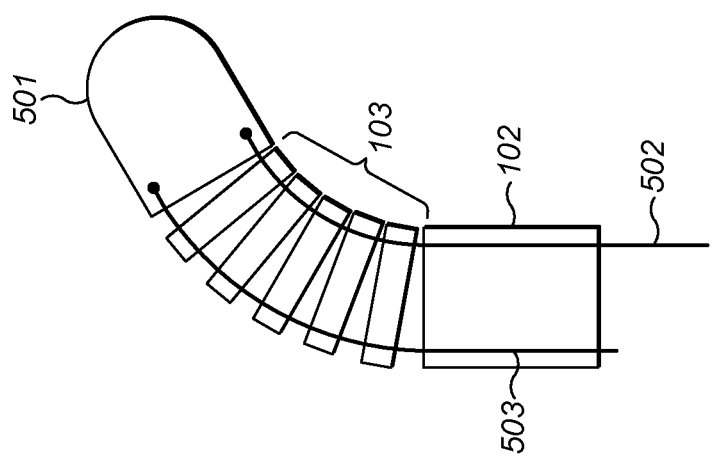
Figure 5A:
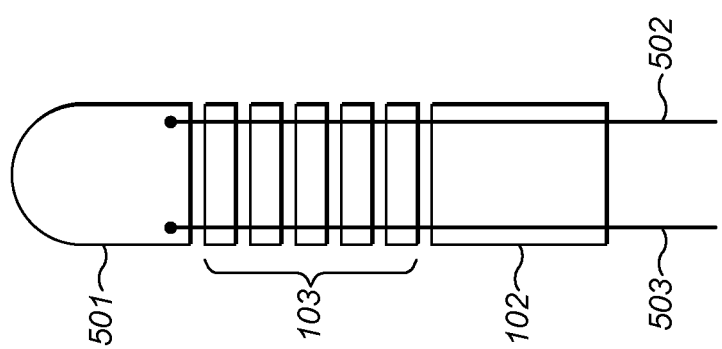

Facing surfaces of adjacent annular rings may be separated by light springs. For example, the light springs may have a spring constant between 0.1 N/mm and 1 N/mm. These light springs ensure that as the articulated section bends to a configuration such as that of FIG. 7*b* or 7*c*, the annular rings are evenly spaced out over the articulated section. The light springs are not strong enough to on their own prevent the configuration of FIG. 5*c* from developing.

In the configurations shown in FIGS. 7*a*, 7*b* and 7*c*, the drive mechanism orients the instrument tip to a desired position by tensioning and (optionally) compressing the driving elements in a controlled manner. The drive mechanism always retains at least one driving element in full tension. This causes the articulated section 103 to always be fully compressed along at least one extent by which it connects the instrument tip and the shaft. This full compression is at the exterior edge of the articulated section along the portion which is closest to the driving element under full tension. Thus, for a given angular relationship between the instrument tip and the shaft, the length of the articulated section is minimised along at least one extent. The length of the articulated section is the separation of the head of the shaft 614 and the base of the instrument tip 615. The length of the articulated section is minimised along the direction in which the annular rings are in contact. The articulated section always has this same minimum length in one extent whichever orientation the instrument tip is in. This is because the articulated section is always fully compressed, and hence at its shortest length along at least one extent. The articulation section is always fully compressed along the inside edge of the bend both when in a configuration such as those shown in FIGS. 7*a*, 7*b* and 7*c*, and also when being moved from one configuration to another configuration.

The drive mechanism thus enables movement of the articulated section so as to permit the instrument tip to move with two degrees of rotational freedom relative to the shaft. Thus, the instrument tip is controllable by the drive mechanism via the articulated section to rotate about axes in a plane transverse to the longitudinal axis of the shaft. Three driving elements enable this rotation. The drive mechanism constrains the movement of the articulated section so as to not permit the instrument tip to move with translational freedom relative to the shaft. Thus, the drive mechanism constrains the movement of the articulated section such that there is never more than one curve in the profile of the articulated section. Thus, the misaligned configuration of FIG. 5*c* does not arise. By controlling the lengths of the driving elements 611, 612, 613, the location and orientation of the instrument tip is controlled. If the driving elements are all the same length, then the articulated section takes the configuration shown in FIG. 7*a* in which the longitudinal axis 701 of the instrument tip 601 is collinear with the longitudinal axis 702 of the shaft 102. This control of the instrument tip 601 is achieved without requiring the driving elements or the annular rings of the articulated section to be sprung. If the annular rings are lightly sprung apart, then this is only to maintain even separation of the annular rings when in a bent configuration such as that of FIG. 7*b* or FIG. 7*c*. The light springs do not provide a sufficient spring force to prevent the misaligned configuration of FIG. 5*c* from occurring.

A respective strain gauge may be attached to each driving element. Each strain gauge measures the tension on the driving element that it is attached to. Optionally, one or more strain gauge may also be attached to the instrument shaft. The strain gauges output their measured tensions to a controller. The controller maintains a model of the instrument system. The controller is a computer-based device which comprises a processor and non-transient computer-readable media such as a memory for storing computer executable instructions. The processor processes the computer executable instructions in order to control the operation of the drive mechanism of the instrument. The controller stores the current position and orientation of the instrument tip as well as the measured tensions of each of the driving elements, and optionally the measured tension of the instrument shaft. The controller receives a desired position of the instrument tip. This may be received, for example, from a user input. The controller determines the tensions to be applied to the driving elements in order to change the orientation of the instrument tip to the desired position. The controller makes this determination with reference to the model which maps tensions of the driving elements to positions of the instrument tip. The tensions determined by the controller to be applied to the driving elements are so as to maintain the instrument shaft in compression and so as to maintain at least one of the driving elements in full compression.

The desired tensions of the driving elements are signalled to the drive mechanism in the instrument base. The controller may signal the actual desired tensions of the driving elements to the drive mechanism. Alternatively, the controller may signal an indication of the desired tensions of the driving elements. For example, the controller may send a control signal which causes a motor to wind a spool by a certain amount. As another example, the controller may send a control signal which causes a motor to wind a screw by a certain amount. The drive mechanism receives the signalling, and implements the instructions. This causes the driving elements to be tensioned and compressed by the amounts determined by the controller.

The controller may signal the drive mechanism to tension a driving element, but not specify how much by. The drive mechanism receives this signal, and pulls the driving element. The strain gauge attached to that driving element measures the tension of that driving element and outputs it to the controller. On determining that the desired tension of the driving element has been reached, the controller may signal the drive mechanism to maintain the current tension on the driving element. In response, the drive mechanism stops further tension from being applied to the driving element, and maintains the current tension on the driving element.

By controlling the movement of the driving elements according to a stored model of the distal end of the instrument, full compression of the articulated section along at least one extent by which it connects the instrument tip and the shaft is ensured.

Full compression of the articulated section along at least one extent by which it connects the instrument tip and the shaft may be ensured by directly sensing the contact between facing surfaces of adjacent annular rings of the articulated section. Contact sensors located on the articulated section sense this contact, and output the sensed contact to the controller. The controller may signal the drive mechanism to displace the driving elements. The drive mechanism receives this signal, and displaces the driving elements as instructed. When the controller receives output from the contact sensors verifying that full compression of the articulated section is achieved, it signals the drive mechanism to maintain the current tension on the driving element. In response, the drive mechanism stops further tension from being applied to the driving element, and maintains the current tension on the driving element.

The attachment 602 may be rigidly attached to the instrument tip 601. Alternatively, the attachment 602 may be connected to the instrument tip 601 by a roll joint. In this case, the controls for the roll joint (for example flexible rods or cables) pass up the inside of the shaft 102 and articulated section 103. The controls for the end effector (for example flexible rods or cables) also pass up the inside of the shaft 102 and articulated section 103.

Figure 8:
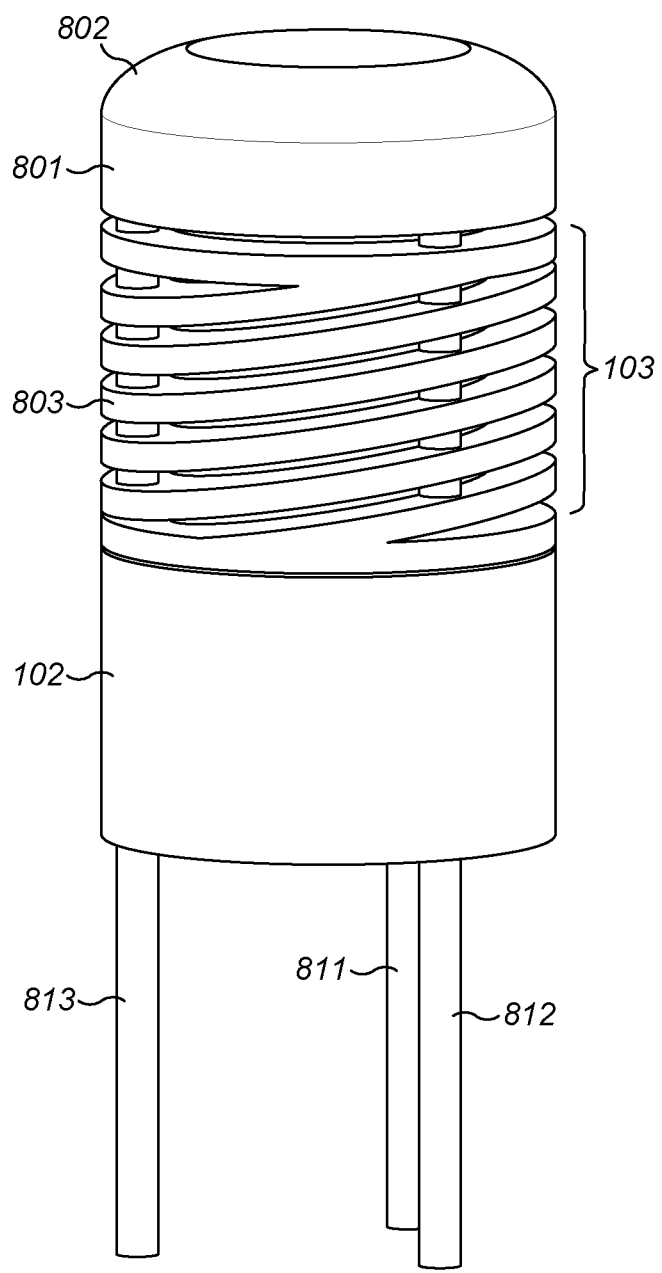
FIG. 8 illustrates the distal end of a further surgical instrument.

The articulated section 103 may be implemented in a different way. For example, the articulated section 103 may comprise a cut spring. The cut spring may be single-start or multi-start. FIG. 8 illustrates an articulated section 103 which is a multi-start helical cut spring 803. The spring is connected at one end to the end of the shaft 102, and at the other end to the instrument tip 801. The outer profile of the spring is aligned with the exterior surfaces of the shaft and tip. The outer profile of the spring is flush with the exterior surfaces of the shaft and tip. The spring is hollow on the inside to enable cables to be passed up through the shaft 102 to the instrument tip 801. The shaft 102, instrument tip 801, attachment 802, and driving elements 811, 812 and 813 are arranged and operate as described with respect to the corresponding components of FIGS. 6, 7a, 7b and 7c. The spring is configured to compress and expand. The spring is able to compress more on one side than another. Thus, the spring enables the instrument tip 801 to be angularly displaced relative to the shaft 102 in a corresponding manner to that illustrated in FIGS. 7b and 7c.

Figure 3:
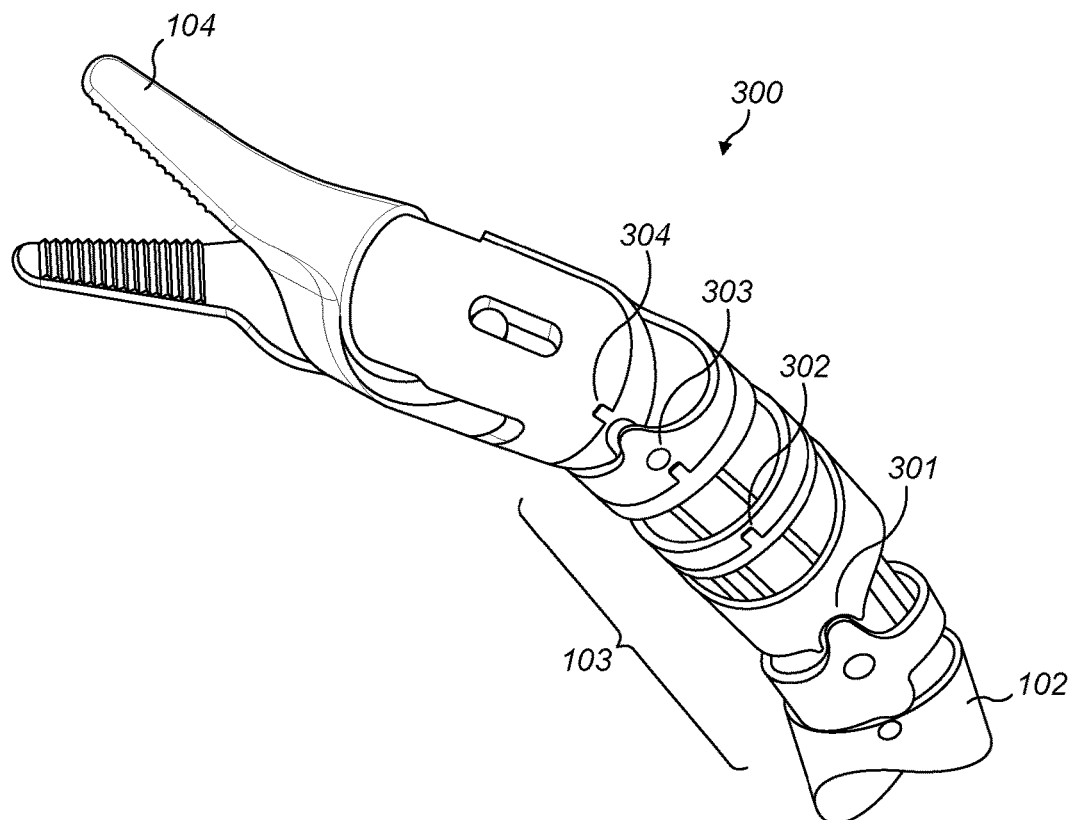
FIG. 3 illustrates a known robotic surgical instrument having a flexible section with independently controlled joints.
Figure 4:
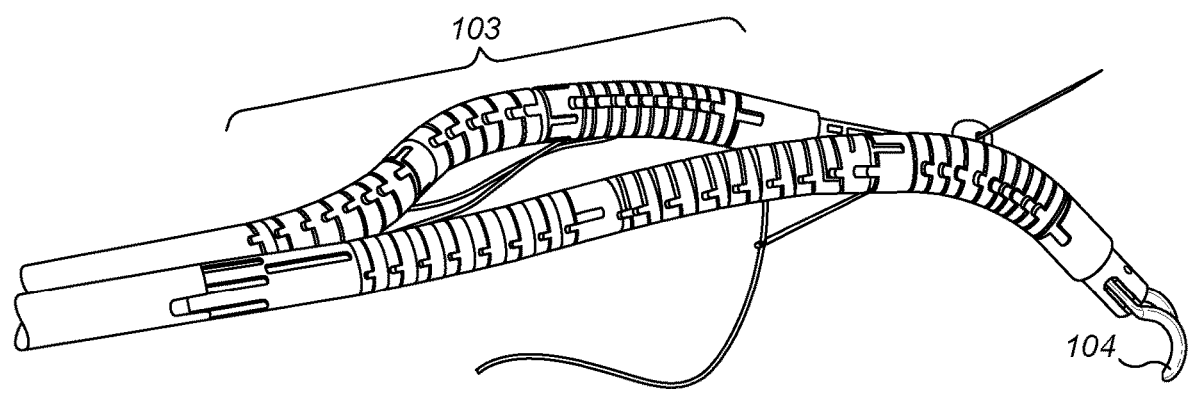
FIG. 4 illustrates a known robotic surgical instrument having a flexible section which is jointly controlled.

The instrument described with respect to FIGS. 6, 7a, 7b, 7c and 8 enables two degrees of freedom in the wrist which are controllable as a result of the manner in which the articulated section 103 is constrained to move. Only three driving elements are required to achieve this motion. The articulated flexible section comprises annular rings or a spring which are less complex, not as small and do not need to be as precisely made as the internal components of the flexible section in FIG. 3. Thus, the external diameter of the instrument can be made to be 5 mm. No sprung forces acting on the articulated section are required to achieve the control described.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument comprising:
a shaft;
a compressible articulated section comprising a plurality of segments extending from the shaft and terminating at a distal end in a tip, the tip having an attachment for an end effector, where the attachment is connected to the tip by a roll joint; and
a drive mechanism configured to drive the articulated section via flexible driving elements thereby altering an angular orientation of the tip relative to the shaft, wherein the drive mechanism is configured to be controlled so as to always fully compress the articulated section along at least one extent at an exterior edge of the articulated section by which the articulated section connects the tip and the shaft whilst driving the articulated section from any one configuration to any other configuration, wherein the drive mechanism constrains movement of the articulated section so as to permit the tip to move with two degrees of rotational freedom and no degrees of translational freedom relative to the shaft.

2. The robotic surgical instrument as claimed in claim 1, wherein the drive mechanism constrains movement of the articulated section so as to permit the tip to rotate about axes in a plane transverse to a longitudinal axis of the shaft.

3. The robotic surgical instrument as claimed in claim 1, wherein the flexible driving elements extend through the shaft, engage with the articulated section and terminate in the tip.

4. The robotic surgical instrument as claimed in claim 1, wherein the drive mechanism is configured to always retain at least one flexible driving element in full tension.

5. The robotic surgical instrument as claimed in claim 1, wherein in a configuration in which a longitudinal axis of the tip is collinear with a longitudinal axis of the shaft, the drive mechanism is configured to retain all the flexible driving elements in full tension.

6. The robotic surgical instrument as claimed in claim 1, wherein in a configuration in which a longitudinal axis of the tip is not collinear with a longitudinal axis of the shaft, the drive mechanism is configured to retain only one flexible driving element in full tension.

7. The robotic surgical instrument as claimed in claim 6, wherein in the said configuration, the drive mechanism is configured to retain at least one other flexible driving element in compression.

8. The robotic surgical instrument as claimed in claim 1, wherein the flexible driving elements resist compression and tension forces.

9. The robotic surgical instrument as claimed in claim 1, comprising at least three flexible driving elements.

10. The robotic surgical instrument as claimed in claim 1, wherein the plurality of segments of the articulated section comprises a single-start helical cut spring, or, a multi-start helical cut spring.

11. The robotic surgical instrument as claimed in claim 1, further comprising strain gauges, each strain gauge configured to measure a tension on a respective flexible driving element.

12. The robotic surgical instrument as claimed in claim 11, wherein the drive mechanism is configured to displace a flexible driving element until that flexible driving element has a desired tension.

13. The robotic surgical instrument as claimed in claim 12, wherein the drive mechanism is configured to receive the desired tension from a controller, the desired tension determined according to a model of current and desired orientations of the tip and the tensions of the flexible driving elements.

* * * * *